(12) United States Patent
Santori et al.

(10) Patent No.: US 9,529,128 B2
(45) Date of Patent: Dec. 27, 2016

(54) NON-UNIFORM GRATING

(75) Inventors: Charles M. Santori, Palo Alto, CA (US); David A. Fattal, Mountain View, CA (US)

(73) Assignee: Hewlett Packard Enterprise Development LP, Houston, TX (US)

( * ) Notice: Subject to any disclaimer, the term of this patent is extended or adjusted under 35 U.S.C. 154(b) by 727 days.

(21) Appl. No.: 13/640,420

(22) PCT Filed: Apr. 26, 2010

(86) PCT No.: PCT/US2010/032448
§ 371 (c)(1),
(2), (4) Date: Oct. 10, 2012

(87) PCT Pub. No.: WO2011/136759
PCT Pub. Date: Nov. 3, 2011

(65) Prior Publication Data
US 2013/0032734 A1 Feb. 7, 2013

(51) Int. Cl.
*G02B 5/18* (2006.01)
*G01N 21/64* (2006.01)
(Continued)

(52) U.S. Cl.
CPC .......... *G02B 5/1866* (2013.01); *G01N 21/6456* (2013.01); *G02B 5/18* (2013.01); *G02B 5/1838* (2013.01); *G02B 19/0009* (2013.01); *G02B 19/0052* (2013.01); *G02B 27/0944* (2013.01); *G01N 21/636* (2013.01); *G01N 21/87* (2013.01); *G01N 2021/646* (2013.01); *G01N 2201/0635* (2013.01)

(58) Field of Classification Search
CPC ....... G02B 5/18; G02B 5/1814; G02B 5/1819; G02B 5/1828; G02B 5/1866; G02B 6/02057; G02B 6/02076; G02B 6/02085; G02B 2006/0209; G01N 21/25
USPC .................. 359/573, 575, 558, 574
See application file for complete search history.

(56) References Cited

U.S. PATENT DOCUMENTS 4,743,083 A * 5/1988 Schimpe ................... 385/37
5,825,448 A * 10/1998 Bos .................. G02F 1/133753
                                                    349/128
(Continued)

FOREIGN PATENT DOCUMENTS

KR    10-20080009280    1/2008

OTHER PUBLICATIONS

Berseth, C. -A. et al. 'Vertical cavity surface emitting lasers incorporating structured mirrors patterned by electron-beam lithographY', J. Vac. Sci. Technol. B, Nov. 1999, vol. 17, No. 6, pp. 3222-3225. See col. 1, lines 11-30; col. 8, lines 2-20; figures 1-7.
(Continued)

*Primary Examiner* — William R Alexander
(74) *Attorney, Agent, or Firm* — Law Office of David T. Millers

(57) ABSTRACT

A system includes a non-uniform grating having a first region with a first refractive index and second regions with a second refractive index. A pattern of the second regions varies with an angular coordinate such that phase shifts of an incident beam created by the grating cause destructive interference that creates an intensity minimum within an output beam from the grating.

19 Claims, 3 Drawing Sheets

(51) Int. Cl.
  *G02B 27/09* (2006.01)
  *G02B 19/00* (2006.01)
  *G01N 21/63* (2006.01)
  *G01N 21/87* (2006.01)

(56) References Cited

U.S. PATENT DOCUMENTS

| | | | | |
|---|---|---|---|---|
| 5,982,334 | A * | 11/1999 | Manasson | H01Q 13/28 343/700 MS |
| 6,807,339 | B1 * | 10/2004 | Tsai | B82Y 20/00 385/24 |
| 2006/0193550 | A1 * | 8/2006 | Wawro | G01N 21/648 385/12 |
| 2006/0262250 | A1 | 11/2006 | Hobbs | |
| 2007/0057211 | A1 * | 3/2007 | Bahlman | G01N 21/6452 250/584 |
| 2008/0138013 | A1 * | 6/2008 | Parriaux | G02B 5/1814 385/37 |
| 2008/0165399 | A1 * | 7/2008 | Ushiro | G02B 1/02 359/15 |
| 2009/0046298 | A1 * | 2/2009 | Betzig | G01N 21/6445 356/521 |
| 2009/0237501 | A1 * | 9/2009 | Lemmer et al. | 348/79 |

OTHER PUBLICATIONS

Chang-Hasnain, C. J. et al. 'Tunable VCSEL Using High Contrast Grating', OSACLEO2009, May 2009.

Chase, C. et al. 'NEMO Tunable VCSEL using Ultra Compact High Contrast Grating for High Speed Tuning', IEEE 21st International Semiconductor Laser Conferenee, Sep. 2008, pp. 161-162.

PCT Search Report, Dec. 29, 2010, PCT/US2010/032448, Filed Apr. 26, 2010.

Rittweger, E. et al., "STED Microscopy reveals crystal colour centres with nanometric resolution" Nature Photonics, vol. 3, pp. 144-147 (2009).

* cited by examiner

NON-UNIFORM GRATING

BACKGROUND

Stimulated Emission Depletion (STED) imaging or microscopy can allow imaging with resolution much smaller than the wavelength of light used. STED imaging generally employs a pair of light beams, i.e., an excitation beam and a depletion beam, which can be simultaneously projected onto a spot on an object containing a fluorescent substance (e.g., containing proteins that are tagged with a fluorescent marker). The excitation beam has a frequency that excites the fluorescent substance so that presence of the fluorescent substance can be identified from emission of fluorescent light. In particular, the excitation beam excites atoms or molecules of the fluorescent substance to a higher energy state, from which molecules can decay and emit light of a characteristic wavelength, which is generally longer than the wavelength of the excitation beam. The excitation beam by itself can be tightly focused onto the target spot, so that the amount of fluorescent substance in the target spot can be determined from the intensity of fluorescent light emitted if the excitation beam is used by itself. However, the minimum area illuminated by the focused excitation beam is diffraction limited and generally has a minimum dimension on the order of the wavelength of the excitation beam, which limits the resolution of an image created solely using the excitation beam and fluorescence detection.

The depletion beam for STED imaging has a wavelength selected to stimulate specific emissions from the fluorescent substance to thereby deplete the population of the fluorescent substance in the excited state that provides the measured fluorescence. As a result, an area of an object illuminated with a sufficient intensity of the depletion beam will not fluoresce at the target frequency when simultaneously exposed to the excitation beam, even if the fluorescent substance is present in the illuminated area. STED imaging can achieve a small spot size and therefore high (e.g., sub-wavelength) resolution using a doughnut-shaped intensity profile for the depletion beam. If both the excitation beam and the doughnut-shaped depletion beams illuminate an area of an object, the measured fluorescence is only significant where the intensity of the excitation beam is high relative to the depletion beam (e.g., in the hole of the doughnut-shaped intensity profile of the depletion beam). The area in which the excitation beam is sufficiently intense relative to the depletion beam can be made much smaller than the area of a diffraction-limited Guassian beam profile. Accordingly, STED imaging has achieved image resolutions down to about 20 nm using light with wavelength of about 600 nm.

STED imaging needs an optical system capable of producing a depletion beam with a doughnut-shaped beam profile. Such a beam profile can be achieved using a spiral zone plate, which applies to a beam a phase shift that varies linearly across a $2\pi$ range as a function of an angle around a central axis. Using current technology, a spiral zone plate generally uses plate thickness to create phase shifts and has a thickness that varies continuously with angle. These spiral zone plates can be difficult to fabricate using current semiconductor processing techniques.

BRIEF DESCRIPTION OF THE DRAWINGS

Use of the same reference symbols in different figures indicates similar or identical items.

DETAILED DESCRIPTION

In accordance with an aspect of the invention, a non-uniform grating has a duty cycle or period that varies with angle as required to act as a spiral phase plate or otherwise to produce a doughnut-shaped intensity profile in an output beam. In these gratings, the duty cycle and period in diffractive regions near a point having coordinates (r,φ) determine the phase shift for light of a target wavelength passing through or reflected at that point, and the duty cycle or period of the grating can be varied as required to produce a phase shift that varies with an angular coordinate φ in a manner that causes total destructive interference of light output from the grating at a central axis of the grating. For example, the phase shift produced by the grating can vary linearly across a $2\pi$ range as angular coordinate φ varies from 0 to $2\pi$. The variation in duty cycle or period can be applied to grating patterns based on concentric rings, parallel lines, or arrays of two dimensional areas. STED imaging systems can use these non-uniform gratings to shape the intensity profile of a depletion beam.

In accordance with a further aspect of the invention, the variation in the phase shift of a grating used to create a doughnut-shaped intensity profile may further depend on a radial coordinate r (e.g., to produce a phase shift proportional to the square $r^2$ of the radius r) and thereby focus the doughnut-shaped intensity profile. Further, in an ideal case, the grating can apply the destructive spiral phase shift at a first wavelength (the wavelength of the depletion laser) but not at a second wavelength (the wavelength of the excitation laser), so that the same integrated optical element or grating can be used to shape the depletion beam profile and simultaneously focus the depletion and excitation beams.

Figure 1:
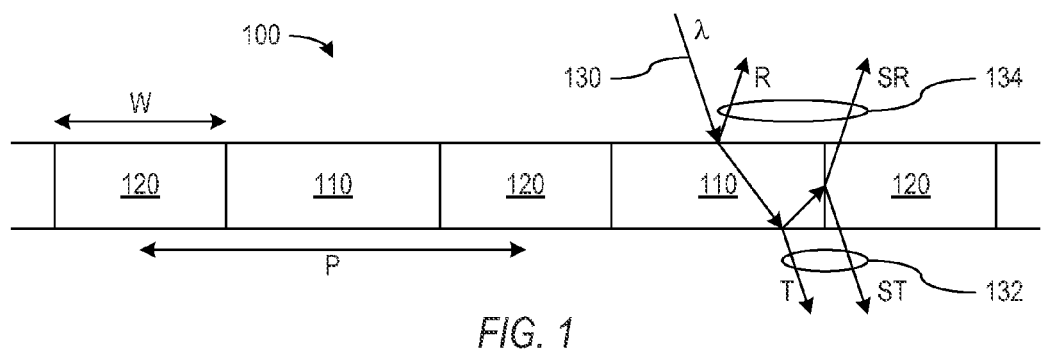
FIG. 1 shows a cross-section of a grating in accordance with an embodiment of the invention.

FIG. 1 shows a cross-sectional view of a sub-wavelength grating (SWG) 100 in accordance with an embodiment of the invention. SWG 100 includes a substrate 110 with regions 120 that differ in refractive index from the rest of substrate 110. In an exemplary embodiment, regions 120 are air gaps, for example, holes that extend through substrate 110 or grooves that extend to a desired depth in substrate 110. Alternatively, regions 120 may contain a solid material that differs in refractive index from substrate 110. The material used for substrate 110 in general is selected depending on the wavelength of light to be used and may, for example, be a quartz plate for visible light or silicon for infrared light. Some other materials that could be used in substrate 110 include but are not limited to silicon nitride, silicon carbide, gallium phosphide, titanium dioxide, zinc selenide, gallium nitride, and sapphire. Alternatively, substrate 110 may be a multi-layer structure, for example, a quartz substrate with an overlying layer of silicon that is patterned to create grooves corresponding to regions 120 in the silicon layer. Substrate 110 may also include cladding or antireflective layers selected to alter the resonance or interference behavior for SWG 100.

Cross-sections of substrate 110 and regions 120 are shown in FIG. 1, and regions 120 can have a variety of patterns across the area of substrate 110. For example, in a line grating, regions 120 correspond to a set of substantially parallel lines or grooves. Alternatively, regions 120 can correspond to concentric rings or areas arranged in an array. In each of these layouts of regions 120 on substrate 110, a period P of the grating can be defined as the center to center spacing of regions 120, and a duty cycle of the grating can be defined as the ratio W/P of the width W of a region 120 to the period P. Typically, SWG 100 is designed for use with light having a specific wavelength $\lambda$ that is longer than width W or period P. As described further below, period P, width W, or duty cycle W/P in SWG 100 are non-uniform and therefore vary in the pattern of regions 120 laid out across the area of SWG 100.

The desired pattern of regions 120 can be created in or on substrate 110 using techniques that are well known in the field of integrated circuit fabrication or nanodevice fabrication. For example, electron beam lithography can directly etch regions 120 as grooves in substrate 110 having size and spacing smaller than the wavelength of visible light. Alternatively, mask and etch processes with a mask created using nanoimprint lithography or conventional photolithography can define the pattern of regions 120. Nanoimprint lithography, for example, uses a mold to create a pattern in a resist layer that expose regions of substrate 110 to etching and can currently achieve feature size down to a few tens of nanometers or less. In an alternative embodiment of the invention, it may be possible to process or chemically treat substrate 110 to give regions 120 a different refractive index from the rest of substrate 110, although air gaps generally provide high refractive index contrast and may be preferred for regions 120.

SWG 100 when illuminated by a monochromatic light beam 130 of wavelength $\lambda$ from a target direction has a first-order diffracted mode that corresponds to a guided wave trapped in substrate 110. Regions 120 scatter light from the trapped wave, and the scattered light can interfere with directly reflected or transmitted light to create a pronounced modulation of transmitted light beam 132 and reflected light beam 134. For example, FIG. 1 illustrates transmitted light beam 132 as including a directly transmitted component T and a scattered component ST and illustrates reflected light beam 134 as including a directly transmitted component T and a scattered component ST. When regions 120 provide a high-index-contrast from substrate 110, regions 120 rapidly scatter the guided waves, so that guided waves do not laterally propagate past many regions 120 in substrate 110. In this case, SWG 100 can be thought of as a coupled resonator system, where grooves or regions 120 define lossy cavities.

The pattern of regions 120 can be selected to produce broad transmission and reflection features for a range of wavelengths and/or resonant behavior at the specific wavelength $\lambda$ and incident direction of incident light 130. For example, the pattern of regions 120 can cause total destructive interference of transmitted components T and ST, effectively eliminating transmitted beam 132, for a highly reflective mirror at a particular frequency or to cause total destructive interference of reflected components R and SR, effectively eliminating reflected beam 134, for a high transmission grating. In an exemplary embodiment, which is described herein to provide a specific example, SWG 100 is highly reflective of beam 130, and a non-uniform pattern of regions 120 is used to control the phase front of reflected beam 134, preferably without affecting the high reflectivity of SWG 100. However, SWG 100 could alternatively be a transmission grating that employs a non-uniform pattern of regions 120 to control the phase from of transmitted beam 132.

A grating that imprints a particular phase profile on an output beam can be understood by considering the spatial scaling properties of Maxwell's equations and gratings. In particular, if the spatial dimensions of a periodic grating are scaled uniformly by a factor $\alpha$, the scaled grating will have a reflection or transmission coefficient profile that varies with wavelength in the same manner as the original or reference grating, but with a wavelength axis that has also been scaled by factor $\alpha$. For example, if a reference grating has a particular complex reflection coefficient $r_0$, at a wavelength $\lambda_0$, then the scaled grating has the same reflection coefficient $r=r_0$ at a wavelength $\lambda$ such that the factor $\alpha$ is equal to the wavelength ratio $\lambda/\lambda_0$. Thus, the complex reflection coefficient $r(\lambda)$ of the scaled grating as a function of wavelength is equal to the reflection coefficient $r_0(\lambda/\alpha)$. The relationships that apply to gratings that differ by a uniform scaling can also apply to non-uniform scaling of gratings with high refractive index contrast. In particular, the reflection properties of a high-contrast SWG at a given point on the SWG critically depend on the local geometry around that point because high-contrast SWGs effectively operate with localized resonances. Accordingly, a non-uniform scaling that varies slowly when compared to the period of a grating can be used to locally tune the complex reflection coefficient of a non-uniform grating to any value in a range of reflection coefficients provided by a reference periodic grating on which the non-uniform grating is based.

A periodic grating that is highly reflective at a wavelength $\lambda$ generally has a range of wavelengths at which the grating is highly reflective, i.e., at which a complex reflection coefficient $r_0$ has a magnitude about equal to 1, e.g., $|r_0| \geq 0.98$. If the wavelength range for high reflectivity is relatively broad, the reference grating may provide a full $2\pi$ or more range of phase shift in the reflected beam. A non-uniform or local scaling of such a reference grating can thus allow local tuning of the reflected phase to any value in the $2\pi$ or more range while maintaining high reflectivity for a monochromatic incident beam. To imprint a phase shift $\Phi(r,\phi)$ on a reflected beam at some point $(r,\phi)$ on the area of a grating, the grating pattern near the point $(r,\phi)$ can be given a scale factor $\alpha(r,\phi)$ relative to the reference grating that provides the desired reflected phase $\Phi(r,\phi)$. Scale factor $\alpha(r,\phi)$ in general will depend on the global pattern (e.g., whether the reference grating is a line grating, a ring grating, or a 2-D gating), the contrast between the refractive indexes of regions 110 and 120, and the characteristics (e.g., frequency, polarization, and direction) of the incident light. A non-uniform SWG with a slowly-varying scale factor $\alpha(r,\phi)$ behaves locally as though the SWG was a periodic grating with a reflection coefficient $r=r_0[\lambda/\alpha(r,\phi)]$, where $r_0[\lambda/\alpha(r,$ φ)] is the reflection coefficient of the reference grating for light of wavelength $\lambda/\alpha(r,\phi)$. Therefore, given a periodic reference grating with a phase shift $\Phi_0$ at some wavelength $\lambda_0$, choosing a local scale factor $\alpha(r,\phi)$ equal to $\lambda/\lambda_0$ where $\lambda$ is the wavelength of incident light on the non-uniform gating will set reflected phase shift $\Phi(r,\phi)$ for the non-uniform gating equal to $\Phi_0$. Thus, so long as all required values of phase changes $\Phi(r,\phi)$ are available within the high-reflectivity spectral window of the reference periodic grating, a non-uniform grating can be created to produce a specific phase map $\Phi(r,\phi)$. Similarly, a desired phase shift profile $c\Phi(r,\phi)$ can be achieved through non-uniform variation in the duty cycle or period of a grating.

Figure 2:
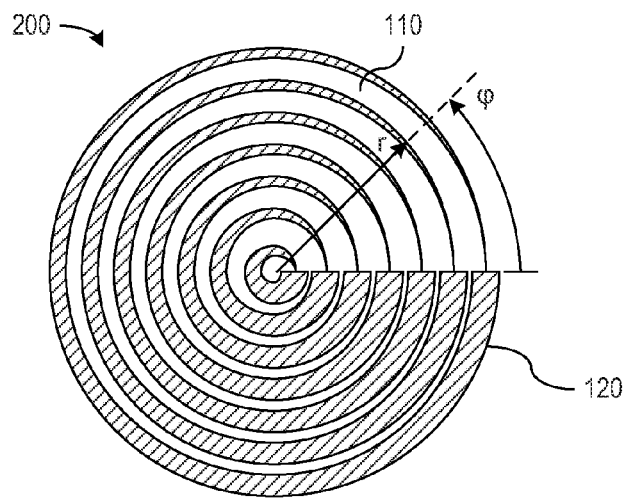
FIG. 2 shows a concentric grating pattern for a non-uniform grating in accordance with an embodiment of the invention.

FIG. 2 shows a plan view of an SWG 200 in accordance with an embodiment of the invention based on a reference grating that is a ring grating. In SWG 200, regions 120 are concentric rings with each ring having a width W (and duty cycle) that increases with an angular coordinate $\phi$, while the period P (or center-to-center spacing of the rings) remains constant. In an exemplary embodiment, the increase in width W can be selected so that the reflected phase shift $\Phi(r,\phi)$ increases linearly over a $2\pi$ range as angular coordinate $\phi$ runs from 0 to $2\pi$, causing SWG 200 to act as a reflective spiral zone plate. As is well known, when an incident beam has a typical intensity distribution, e.g., a Gaussian intensity profile, the overlap and interference of the $2\pi$ range in phase shifts of the output beam near the center axis of a spiral zone plate causes nearly total destructive interference, but the destructive interference decreases with distance from the center to provide a doughnut-shaped beam profile for the output beam. More generally, when a doughnut-shaped intensity profile is needed, SWG 200 does not need to provide a linear increase of phase shift over a $2\pi$ range, but can provide any variation in output phase with angular coordinate $\phi$ such that superposition of light around the range of coordinate $\phi$ provides the desired level of destructive interference.

The pattern of regions 120 in SWG 200 can use several alternative scaling methods to achieve the same or similar effects at the desired incident wavelength. In the illustrated embodiment, the width or duty cycle of regions 120 are scaled, while the period of regions remains constant. Alternatively, period of regions 120 can be non-uniformly scaled to increase or decrease with angular coordinate $\phi$, which will convert rings into spirals. Also, the widths of the spirals may be scaled by the same angle-dependent factor as the period, by a different factor from the period, or not scaled, although the local phase change produced generally depends on both the width and period for a fixed refractive index difference. As a result of monotonically increasing the width in the illustrated embodiment of FIG. 2, ring-shaped regions 120 have a discontinuity in width W along the ray corresponding to angular coordinate $\phi$ having value 0 or $2\pi$. However width W is not required to monotonically increase but may, for example, increase in width to create a range of phase equal to an integer multiple of $2\pi$ as angular coordinate $\phi$ ranges from 0 to $\pi$ and decrease in width to create a range of phase equal to an integer multiple of $2\pi$ as angular coordinate $\phi$ ranges from $\pi$ to $2\pi$. This freedom to select the pattern of regions 120 may allow selection of the pattern of regions 120 to provide a first phase shift profile at a first wavelength (e.g., the wavelength of a depletion laser) and provide a second, quite different phase shift profile at a second wavelength (e.g., the wavelength of a excitation laser.)

SWG 200 in general may have polarization dependent phase shifts resulting from the direction of the extended or narrow dimension of regions 120 relative to a polarization direction of the incident light. When the polarization of the incident beam is known and fixed, e.g. known to be a linear polarization in a particular direction, the polarization dependent effects may be taken into account when selecting the variation in the width or period of regions 120. However, for linearly polarized light, polarization effects may be more easily addressed using a non-uniform grating that is based on a line grating layout.

Figure 3:
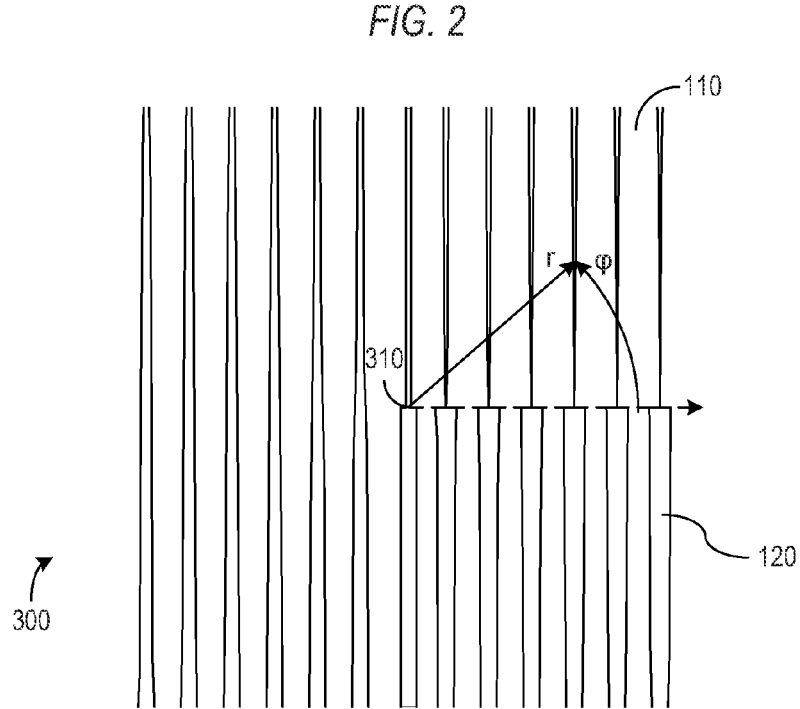
FIG. 3 shows a pattern of parallel lines having widths that vary with an angular coordinate to create a non-uniform grating in accordance with an embodiment of the invention.

FIG. 3 illustrates a non-uniform SWG 300 based on a reference grating that is a periodic line grating. In SWG 300, regions 120 of substrate 110 have center lines with constant orientation (e.g., parallel or perpendicular) relative to the direction of polarization of linearly polarized light. In the illustrated embodiment, regions 120 have uniform spacing or period and non-uniform widths. In particular, each line region 120 has a width at a point $(r,\phi)$ that depends on the value of angular coordinate $\phi$. The variation in the width is more specifically such that an integral of the phase shifts around a circular path near an origin 310 of the r-$\phi$ coordinate system is zero when an input beam is incident at a target angle. As a result, when the incident beam is centered on origin 310, the phase shifted light output very near a central axis of the output beam destructively interferes while light further from the central axis does not, resulting in a doughnut-shaped intensity profile for the output beam. An output beam with a doughnut-shaped intensity profile could alternatively be created using a period or spacing of regions 120 that is non-uniform and has a functional dependence on angular coordinate $\phi$. However, scaling of the period causes regions 120 to curve, possibly introducing direction-dependent polarization effects.

Figure 4:
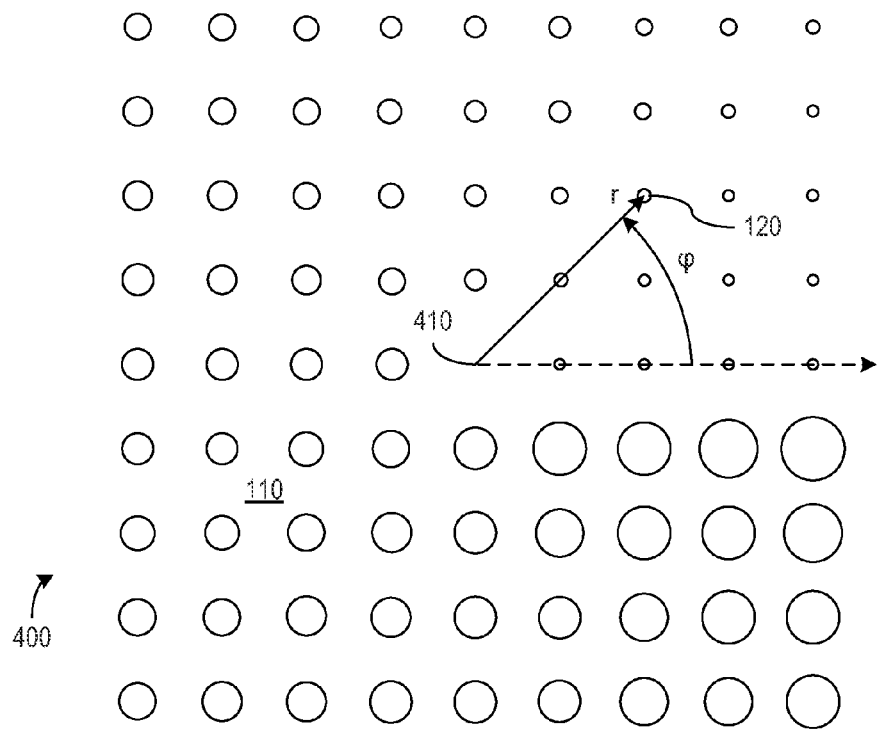
FIG. 4 shows a two-dimensional grating pattern containing an array of regions that vary in size to create a grating in accordance with an embodiment of the invention.

FIG. 4 illustrates an SWG 400 in accordance with an embodiment of the invention based on a two-dimensional grating pattern with uniform spacing of regions 120. Regions 120 in SWG 400 can be cylindrical air gaps that are arranged in a rectangular array with uniform period P. However, regions 120 may have cross-sectional areas other than circular and rather than being air gaps, may be regions of solid material providing a suitable refractive index contrast from substrate 110. The size of each region 120 depends at least on the value of angular coordinate $\phi$ for that region 120. In particular, regions 120 vary in size with angular coordinate $\phi$ in a manner that causes destructive interference of an output beam near a central axis of the output beam when an input beam of a target wavelength $\lambda$ is incident on SWG 400 at a target angle and centered on an origin 410 of the r-$\phi$ coordinate system. For example, the diameters of regions 120 can vary with angular coordinate $\phi$ such that the phase shift in the output beam has a range equal to an integer multiple of $2\pi$ and is linearly dependent on angular coordinate $\phi$. Many other plans for variation in the sizes of regions 120 could be used, and the particular pattern used for regions 120 may be selected not only to achieve destructive interference of light of the target wavelength near the central axis of the output beam but also to provide a desired optical function such as focusing or collimating a light beam having a second frequency. An advantage of SWG 400 is that a two-dimensional array of regions 120 may perform beam profile modification with less dependence on the polarization of the incident beam.

Figure 5:
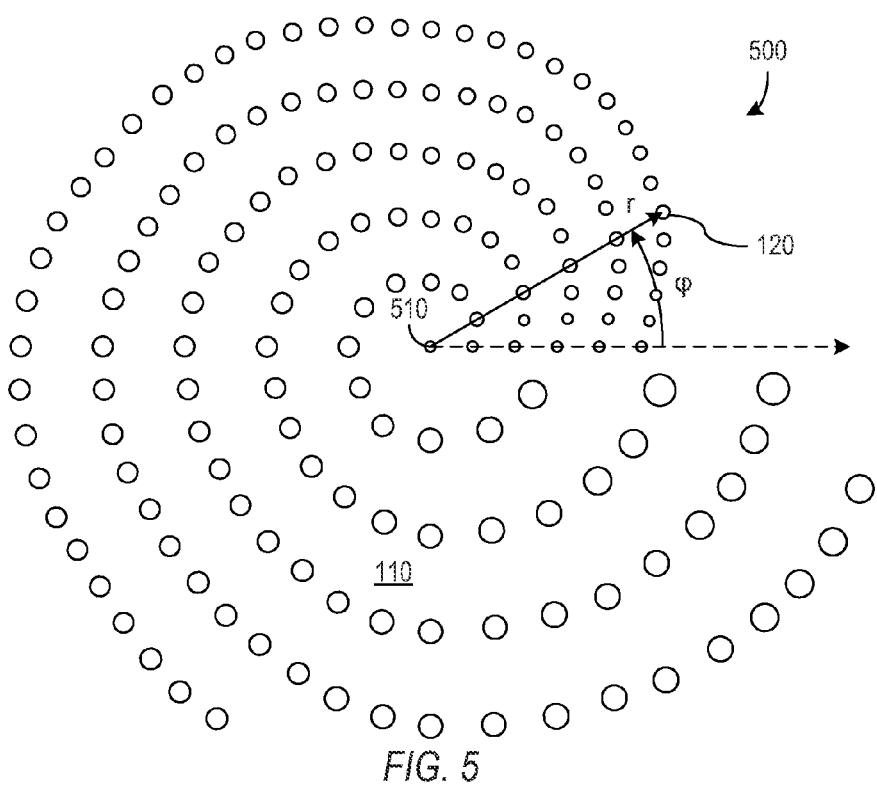
FIG. 5 shows a two-dimensional pattern of regions that vary in size and spacing to create a grating in accordance with an embodiment of the invention.

FIG. 5 illustrates an SWG 500 in accordance with an embodiment of the invention based on a two-dimensional grating pattern with non-uniform spacing and non-uniform size of regions 120. Regions 120 in SWG 500 can again be cylindrical air gaps or differently shaped regions 120 could be used. In SWG 500, both period P and diameter W vary (e.g., increase) with angular coordinate $\phi$ to cause destructive interference on the central axis of the output beam when an input beam is incident at a target angle and centered at the origin 510 of the r-φ coordinate system on SWG 500. FIG. 5 specifically shows an embodiment in which period P and diameter W increase with angular coordinate φ resulting in a set of spirals containing regions 120. Other patterns of regions 120 could be used to achieve the same or similar results.

The gratings of FIGS. 2, 3, 4, and 5 as noted above use a period or duty cycle with non-uniform variation that depends on angular coordinate φ as required to produce destructive interference near the central axis of an output beam. Further, any of the above patterns could have periods or duty cycles that depend on a radial coordinate r in order to produce other desirable optical effects. For example, the variation in the phase shift of a grating may depend on a radial coordinate r (e.g., to produce a phase shift proportional to the square $r^2$ of the radius r) to give the grating focusing power. A system such as a STED imaging system might then be able to reduce part count by using one grating to shape and focus a depletion beam. Further, the destructive interference that provides a very low intensity area within the cross-section of the depletion beam can be highly dependent on the wavelength of the beam. As a result, an input beam with a slightly different wavelength may produce an output beam having a central intensity that is much less attenuated by interference, not at all attenuated, or even enhanced as a result of constructive interference near the area where the intensity of the depletion beam has a minimum. In this case, a single grating might be used in a STED imaging system to shape the depletion beam and to focus both the depletion beam and the excitation beam.

Figure 6:
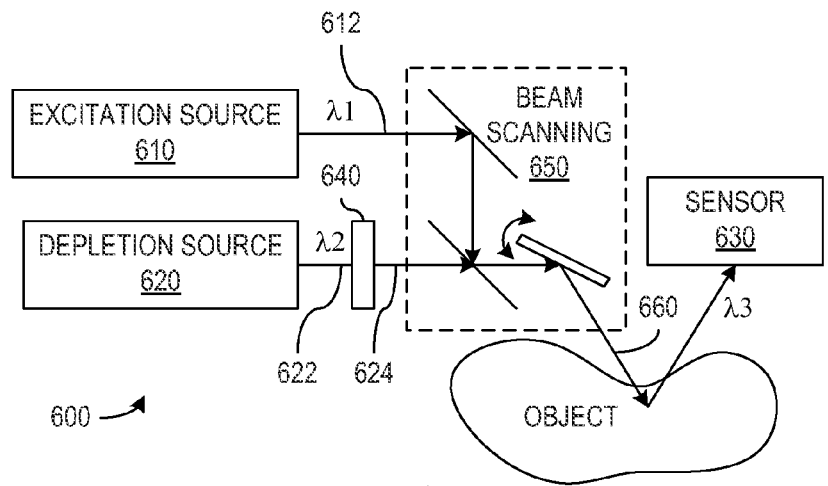
FIG. 6 shows a stimulated emission depletion imaging system that shapes a depletion beam using a grating in accordance with an embodiment of the invention.

FIG. 6 shows an example of a STED imaging system 600 in accordance with an embodiment of the invention. STED imaging system 600 includes an excitation beam source 610, a depletion beam source 620, a light sensing unit 630, a grating 640, and beam scanning optics 650. Excitation and depletion beam sources 610 and 620 can be lasers or other light sources that produce respective monochromatic beams 612 and 622 of light having different wavelengths λ1 and λ2. Wavelength λ1 is selected to raise atoms or molecules of a specific fluorescent substance to an excited energy state that tends to decay and fluoresce by emitting light of wavelength λ3. Wavelength λ2 is selected to stimulate emissions from the excited state of the fluorescent substance without producing light of wavelength λ3. Lasers and most other light sources tend to naturally produce beams having highest intensity at the center of the beam, e.g., with a Gaussian intensity profile.

Grating 640 is a non-uniform sub-wavelength grating such as described above with reference to FIG. 2, 3, 4, or 5 and may be based on a uniform ring, line, or two-dimensional grating. Grating 640 is in the path of the depletion beam in STED system 600 and oriented to transform depletion beam 622 into a depletion beam 624 having a doughnut-shaped intensity profile, which has a central minimum along the propagation axis of beam 624. In FIG. 6, grating 640 appears to be a transmission grating with light incident from a direction normal to the surface of grating 640, but in general, grating 640 can be a reflection or transmission grating that is oriented at an angle relative to beam 622 in order to give beam 624 the desired intensity profile for use in STED imaging system 600. Grating 640 can also serve to focus or collimate depletion beam 624, and/or additional optical elements (not shown) can be used for focusing or collimation of depletion beam 622 or 624. Excitation beam 612 can be similarly focused or collimated using conventional beam optics (not shown.)

Figure 7:
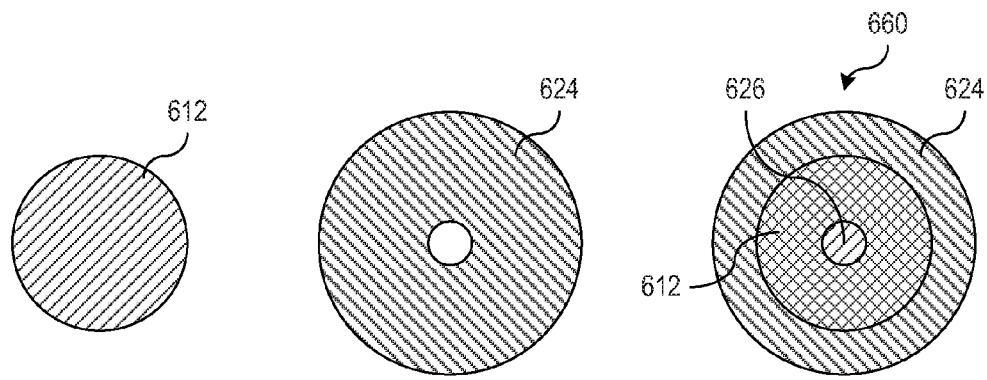
FIG. 7 illustrates beam profiles of an excitation beam, a depletion beam, and a combined beam in a STED imaging system.

Beam scanning system 650 employs conventional optical elements to combine or otherwise direct the excitation and depletion beams for precise overlapping incidence on the object to be imaged. FIG. 7 illustrates the profiles of excitation beam 612, depletion beam 624, and a combined beam 660 on the object being measured. In the illustrated configuration, excitation beam 612 has a circular area in which beam intensity is sufficient to cause fluorescence suitable for imaging, and depletion beam 624 has a doughnut-shaped area in which depletion beam intensity is sufficient to deplete an excited state of the fluorescent substance and prevent fluorescence suitable for imaging. At the surface of the object, beams 612 and 624 overlap in combined beam 660 so that excitation beam 612 is only able to produce fluorescence for imaging from a small area 626 of the object around the intensity minimum within depletion beam 624. Sensing system 630 can measure the intensity of fluorescent light having wavelength λ3 for determination of the concentration of fluorescent substance in the small area 626.

In an exemplary embodiment of the invention, the fluorescent material in the object being imaged is diamond with nitrogen-vacancy defects. With this fluorescent material, excitation wavelength λ1 can be selected from the range between about 500 and 600 nm. The emission wavelength λ3 of the target fluorescence is in a broad band from about 630 to 800 nm, and the depletion wavelength λ2 can be chosen, for example, to be about 775 nm so that most of the spontaneous emission (e.g., from 630 to 750 nm) is available for collection by sensor 630. In general, depletion beam 624 can be a continuous beam, and sensor 630 can include a filter to remove wavelength λ2 from the measured light. Alternatively, depletion beam 624 could be pulsed to permit sensor 630 to measure fluorescence while a combined depletion-excitation beam 660 is off. STED imaging system 600 can construct an extended image of the object by scanning beam 660 across the object while measuring the resulting fluorescence.

Figure 8:
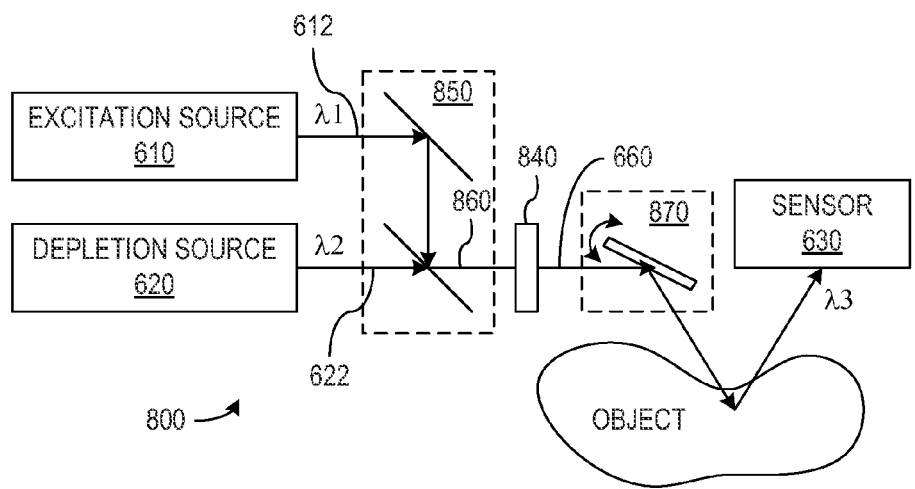
FIG. 8 shows stimulated emission depletion imaging systems that shapes a depletion beam and focuses depletion and excitation beams using a grating in accordance with an embodiment of the invention.

FIG. 8 shows a STED imaging system 800 using a grating 840 to both shape and focus a combined beam 860. In STED imaging system 800, excitation and depletion beam sources 610 and 620 respectively produce excitation and depletion beams 612 and 622 as described above with reference to FIG. 6, but beam optics 850 combine excitation and depletion beams 612 and 622 into combined beam 860 that is incident on grating 840. Grating 840 then shapes the spectral component of combined beam 860 having depletion wavelength λ2 to produce a doughnut-shaped intensity profile in that spectral component and may also focus both spectral components of combined beam 860. As a result, grating 840 can produce the combined beam 660 having the intensity profiles illustrated in FIG. 7. A scanning system 870 can then be used to scan the object using beam 660 while measuring the fluorescent light resulting from illumination of the object by the small central area 626 of combined beam 660.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A system comprising a non-uniform grating having:
   a first region that has a first refractive index; and
   second regions that have a second refractive index,
   wherein in a polar coordinate system that is parallel to a beam-incident-face of the grating, a center-to-center spacing in a radial direction between the second regions varies according to an angular coordinate such that phase shifts created by the grating in an incident beam on the grating cause destructive interference that creates an intensity minimum within an output beam from the grating.

2. The system of claim 1, wherein the output beam has a doughnut-shaped intensity profile.

3. The system of claim 1, wherein the first region comprises a substrate and the second regions comprise air gaps in the substrate.

4. The system of claim 1, wherein each of the second regions is a strip that spirals around the origin of the polar coordinate system and has a width that varies according to the angular coordinate.

5. The system of claim 1, wherein the second regions are arranged in a two-dimensional array.

6. The system of claim 5, wherein sizes of the second regions vary with the angular coordinate.

7. The system of claim 1, wherein a pattern of the second regions varies with a radial coordinate in a manner that focuses the output beam.

8. The system of claim 1, further comprising:
a first light source that produces an excitation beam having a first wavelength;
a second light source that produces a depletion beam that is incident on the grating, the depletion beam having a second wavelength; and
beam optics that combine the excitation beam and an output beam from the grating for projection onto an object being imaged.

9. The system of claim 1, further comprising:
a first light source that produces an excitation beam having a first wavelength;
a second light source that produces a depletion beam having a second wavelength; and
beam optics that combine the excitation beam and the depletion beam to produce a combined beam that is incident on the grating and then projected onto an object being imaged.

10. The system of claim 8, further comprising a sensor arranged to measure fluorescent light originating from the object.

11. The system of claim 1,
wherein the second regions are such that, when a central axis of the incident beam is incident on the beam-incident face of the grating at a point corresponding to an origin of the polar coordinate system, the intensity minimum in the output beam is located on a central axis thereof.

12. The system of claim 5,
wherein the second regions have cross sectional profiles that are circular.

13. A system comprising:
a non-uniform grating that comprises a first region that has a first refractive index and second regions that have a second refractive index,
wherein the second regions are oblong and arranged such that longitudinal centerlines thereof are parallel and uniformly spaced, and
in a polar coordinate system that is parallel to a beam-incident-face of the grating, a width of each of the second regions varies according to an angular coordinate such that phase shifts created by the grating in an incident beam on the grating cause destructive interference that creates an output beam from the grating that has an intensity profile in which a region of lower intensity is surrounded by a region of higher intensity.

14. The system of claim 13,
wherein the widths of the second regions are such that an integral of the phase shifts created by the grating over a circular path around an origin of the polar coordinate system is zero when the incident beam is at a target angle.

15. The system of claim 13,
wherein the widths of the second regions are such that, when a central axis of the incident beam is incident on the beam-incident face of the grating at a point corresponding to an origin of the polar coordinate system, the region of lower intensity in the intensity profile of the output beam corresponds to a central axis of the output beam.

16. A system comprising:
a non-uniform grating that comprises a first region that has a first refractive index and second regions that have a second refractive index,
wherein the second regions are arranged in an array with uniform spacing, and
in a polar coordinate system that is parallel to a beam-incident-face of the grating, the size of each of the second regions varies according to an angular coordinate such that phase shifts created by the grating in an incident beam on the grating cause destructive interference that creates an output beam from the grating that has an intensity profile in which a centralized low intensity region is surrounded by a high intensity region.

17. The system of claim 16,
wherein the sizes of the second regions are such that an integral of the phase shifts created by the grating over a circular path around an origin of the polar coordinate system is zero when the incident beam is at a target angle.

18. The system of claim 16,
wherein the sizes of the second regions are such that, when a central axis of the incident beam is incident on the beam-incident face of the grating at a point corresponding to an origin of the polar coordinate system, the region of lower intensity in the intensity profile of the output beam corresponds to a central axis of the output beam.

19. The system of claim 16,
wherein the second regions have cross sectional profiles that are circular.

* * * * *